United States Patent
Pines et al.

(10) Patent No.: US 6,562,829 B1
(45) Date of Patent: May 13, 2003

(54) TREATMENT OF HEPATIC CIRRHOSIS

(75) Inventors: Mark Pines, Rehovot (IL); Arnon Nagler, Jerusalem (IL)

(73) Assignees: Hadasit Medical Research Services & Development Co., Ltd., Jerusalem (IL); Agricultural Research Organaization-Ministry of Agriculture, Bet Dagan (IL)

( * ) Notice: Subject to any disclaimer, the term of this patent is extended or adjusted under 35 U.S.C. 154(b) by 0 days.

(21) Appl. No.: 09/417,083

(22) Filed: Oct. 13, 1999

Related U.S. Application Data

(63) Continuation of application No. 08/862,382, filed on May 23, 1997, now abandoned, and a continuation-in-part of application No. 09/229,894, filed on Jan. 14, 1999, now abandoned.

(51) Int. Cl.⁷ ............................................. A61K 31/505
(52) U.S. Cl. ...................................................... 514/259
(58) Field of Search ......................................... 514/259

(56) References Cited

U.S. PATENT DOCUMENTS

| | | | |
|---|---|---|---|
| 3,320,124 A | 5/1967 | Waletzky et al. | |
| 3,338,909 A | 8/1967 | Barringer, Jr. et al. | |
| 5,449,678 A | * 9/1995 | Pines et al. .................. | 514/259 |

FOREIGN PATENT DOCUMENTS

WO  WO 96/06616  3/1996

OTHER PUBLICATIONS

Ala–Kokko, L., *Biochem. J.,* 244: 75–79 (1987).
Casas et al., *Ann. Rhem. Dis.,* 46: 763 (1987).
Choi et al., *Arch. Surg.* 130: 257–261 (1995).
Cunliffe et al., *J. Med. Chem.,* 35: 2652 (1992).
Friedman, S.L., *New Eng. J. Med.,* 328: 1828–1835 (1993).
Gascon–Barre et al., *J. Histochem. Cytochem.,* 37: 377–381 (1989).
Hori et al., *Dig. Dis. Sci.,* 38: 2195–2202 (1993).
Jezequel et al., *J. Hepatol.,* 5: 174–181 (1987).
Karvonen et al., *J. Biol. Chem.,* 265: 8415–8419 (1990).
Kershenobich et al., N. Eng. J. Med., 318 1709–1713 (1988).
Kivirikko, *Annals of Medicine,* 25: 113–126 (1993).
Kountaras et al., *Br. J. Exp. Pathol.,* 65: 305–311 (1984).
Krom, M.D., Analyst, 105: 305–316 (1980).
Muller et al., *Exp. Pathol.,* 34: 229–236 (1988).
Muriel et al., *J. Hepatol.,* 21: 95–102 (1994).
Muriel et al., *J. Appl. Tox.,* 15: 449–453 (1995).
Pines et al., *Matrix Biology,* 14: 765–711 (1996).
Salo et al., *J. Oral Pathol. Med.,* 19: 404 (1990).

* cited by examiner

*Primary Examiner*—Jerome D. Goldberg
(74) *Attorney, Agent, or Firm*—Leon R. Yankwich; David G. O'Brien

(57) ABSTRACT

A composition for treating hepatic fibrosis and a method of using and manufacturing the composition are provided. The composition includes a quinazolinone derivative, preferably Halofuginone.

7 Claims, 9 Drawing Sheets

HALOFUGINONE
12 WEEKS

HALOFUGINONE
12 WEEKS

THIOACETAMIDE
12 WEEKS

THIOACETAMIDE
12 WEEKS

HALOFUGINONE - 5ppm in diet
THIOACETAMIDE - 200mg/kg twice a week

THIOACETAMIDE +
HALOFUGINONE
12 WEEKS

THIOACETAMIDE +
HALOFUGINONE
12 WEEKS

HALOFUGINONE - 5ppm in diet
THIOACETAMIDE - 200mg/kg twice a week

TAA
12 WEEKS

TAA
12 WEEKS

TAA 12 WEEKS
+ 8 WEEKS
NO HALIFUGINONE

TAA 12 WEEKS
+ 8 WEEKS
NO HALIFUGINONE

HALOFUGINONE - 5ppm in diet
THIOACETAMIDE - 200mg/kg twice a week

TAA 12 WEEKS
+ 8 WEEKS WITH
HALIFUGINONE

TAA 12 WEEKS
+ 8 WEEKS WITH
HALIFUGINONE

HALOFUGINONE - 5ppm in diet
THIOACETAMIDE - 200mg/kg twice a week

TREATMENT OF HEPATIC CIRRHOSIS

This is a Continuation Application of U.S. patent application Ser. No. 08/862,382, filed on May 23, 1997, now abandoned, and a Continuation-in-Part Application of U.S. patent application Ser. No. 09/229,894, filed on Jan. 14, 1999, currently abandoned.

FIELD AND BACKGROUND OF THE INVENTION

The present invention relates to the treatment of hepatic cirrhosis and, in particular, to the treatment of hepatic cirrhosis with quinazolinone derivatives such as Halofuginone.

Hepatic cirrhosis has a number of causes, including hepatic fibrosis caused by chronic alcoholism, malnutrition, hemochromatosis, passive congestion, hypercholesterolemia, exposure to hepatotoxic chemical substances, exposure to drugs, immune reactions, genetically determined sensitivities to certain substances as seen with copper in Wilson's disease and infections such as viral hepatitis, syphilis and various parasitic infections including, but not limited to, Schistosomiasis mansoni and S. japonica. For reasons given in greater detail below, the disease is currently incurable and frequently fatal.

The pathogenesis of hepatic cirrhosis progresses in a number of stages. First, an enlarged liver is seen with various fatty changes. Next, overt fibrosis is evident with a concomitant decrease in liver function. Finally, atrophy of the liver begins, with a corresponding reduction in the size and functionality of the liver. Necrosis of the liver can be seen at any stage, but is particularly pronounced by late stage cirrhosis. Microscopically, a complete disruption of the normal architecture of the liver is evident.

Outside of the liver, other pathological changes become evident as cirrhosis progresses. Portal circulation is reduced as fibrotic tissue is formed in the liver, further reducing liver functionality. This reduced circulation causes an increase in collateral venous circulation, particularly in the esophagus. These esophageal blood vessels can rupture, causing fatal hemorrhage. Thus, cirrhosis is an entire pathological process with effects that are not limited to the liver, although the root causes can be found in specific pathological changes to the liver itself.

One necessary step in the pathogenesis of hepatic cirrhosis is the formation of fibrotic tissue in the liver. Hepatic fibrosis is a feature of most chronic liver diseases, not just cirrhosis [S. L. Friedman, New Eng. J. Med., 328:1828–35, 1993]. In hepatic fibrosis, connective tissue accumulates in the liver, replacing normal hepatic parenchymal tissue, and reducing liver functionality. The fibrotic tissue replaces more complex normal liver tissue in a pathological process which reduces the amount of liver tissue available for normal functions, such as the removal of toxic substances from the blood, and which progressively disrupts intrahepatic blood flow. The formation of fibrotic tissue in the liver is characterized by the deposition of abnormally large amounts of extracellular matrix components, including at least five types of collagen, in particular collagen types I, III, and IV, as well as other matrix proteins [L. Ala-Kokko, Biochem. J, 244:75–9, 1987].

The synthesis of collagen is also involved in a number of other pathological conditions. For example, clinical conditions and disorders associated with primary or secondary fibrosis, such as systemic sclerosis, graft-versus-host disease (GVHD), lung fibrosis and a large variety of autoimmune disorders, are distinguished by excessive production of connective tissue, which results in the destruction of normal tissue architecture and function. These diseases can best be interpreted in terms of perturbations in cellular functions, a major manifestation of which is excessive collagen synthesis and deposition. The crucial role of collagen in fibrosis has prompted attempts to develop drugs that inhibit its accumulation [K. I. Kivirikko, Annals of Medicine, Vol. 25, pp. 113–126 (1993)].

Such drugs can act by modulating the synthesis of the procollagen polypeptide chains, or by inhibiting specific post-translational events, which will lead either to reduced formation of extra-cellular collagen fibers or to an accumulation of fibers with altered properties. Unfortunately, only a few inhibitors of collagen synthesis are available, despite the importance of this protein in sustaining tissue integrity and its involvement in various disorders.

For example, cytotoxic drugs have been used in an attempt to slow the proliferation of collagen-producing fibroblasts [J. A. Casas, et al., Ann. Rhem. Dis., 46: 763, 1987], such as colchicine, which slows collagen secretion into the extracellular matrix [D. Kershenobich, et al., N. Engl. J. Med., 318:1709, 1988], as well as inhibitors of key collagen metabolism enzymes [K. Karvonen, et al., J. Biol Chem., 265: 8414, 1990; C. J. Cunliffe, et al., J. Med. Chem., 35:2652, 1992].

Unfortunately, none of these inhibitors are collagen-type specific. Also, there are serious concerns about the toxic consequences of interfering with biosynthesis of other vital collagenous molecules, such as Clq in the classical complement pathway, acetylcholine esterase of the neuro-muscular junction endplate, conglutinin and liver surfactant apoprotein.

Other drugs which can inhibit collagen synthesis, such as nifedipine and phenytoin, inhibit synthesis of other proteins as well, thereby non-specifically blocking the collagen biosynthetic pathway [T. Salo, et al., J. Oral Pathol. Med., 19: 404,1990].

Collagen cross-linking inhibitors, such as β-aminopropionitrile, are also non-specific, although they can serve as useful anti-fibrotic agents. Their prolonged use causes lathritic syndrome and interferes with elastogenesis, since elastin, another fibrous connective tissue protein, is also cross-linked. In addition, the collagen cross-linking inhibitory effect is secondary, and collagen overproduction has to precede its degradation by collagenase. Thus, a type-specific inhibitor of the synthesis of collagen itself is clearly required as an anti-fibrotic agent.

Such a type-specific collagen synthesis inhibitor is disclosed in U.S. Pat. No. 5,449,678 for the treatment of a fibrotic condition. This specific inhibitor is a composition with a pharmaceutically effective amount of a pharmaceutically active compound of a formula:

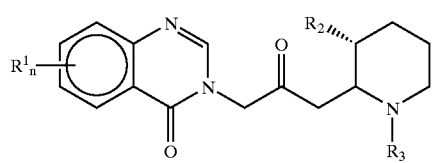

wherein:
$R_1$ is a member of the group consisting of hydrogen, halogen, nitro, benzo, lower alkyl, phenyl and lower alkoxy; $R_2$ is a member of the group consisting of hydroxy, acetoxy and lower alkoxy; and $R_3$ is a member of the group consisting of hydrogen and lower alkenoxy-carbonyl; wherein n is 1 or 2. Pharmaceutically acceptable salts thereof are also included. Of this group of compounds, Halofuginone has been found to be particularly effective for such treatment.

U.S. Pat. No. 5,449,678 discloses that these compounds are effective in the treatment of fibrotic conditions such as scleroderma and GVHD. PCT Application No. WO 96/06616 further discloses that these compounds are effective in treating restenosis. The two former conditions are associated with excessive collagen deposition, which can be inhibited by Halofuginone. Restenosis is characterized by smooth muscle cell proliferation and extracellular matrix accumulation within the lumen of affected blood vessels in response to a vascular injury [Choi et al., *Arch. Surg.*, 130:257–261, 1995]. One hallmark of such smooth muscle cell proliferation is a phenotypic alteration, from the normal contractile phenotype to a synthetic one. Type I collagen has been shown to support such a phenotypic alteration, which can be blocked by Halofuginone [Choi et al., *Arch. Surg.*, 130: 257–261, 1995; U.S. Pat. No. 5,449,678].

However, the in vitro action of Halofuginone does not always predict its in vivo effects. For example, Halofuginone inhibits the synthesis of collagen type I in bone chrondrocytes in vitro, as demonstrated in U.S. Pat. No. 5,449,678. However, chickens treated with Halofuginone were not reported to have an increased rate of bone breakage, indicating that the effect is not seen in vivo. Thus, the exact behavior of Halofuginone in vivo cannot always be accurately predicted from in vitro studies.

Furthermore, the ability of Halofuginone or other related quinazolinone to block or inhibit pathological processes related to hepatic cirrhosis has not been demonstrated. Other inhibitors of collagen synthesis, cross-linking and deposition, such as corticosteroids, penicillamine, methotrexate and colchicine, have been tested for their therapeutic effect on hepatic fibrosis, but have not proved effective [S. L. Friedman, *New Eng. J. Med.*, 328:1828–35, 1993]. Although Halofuginone has been shown to have a specific inhibitory effect on the synthesis of type I collagen, such inhibition has not been otherwise shown to be efficacious in the treatment of hepatic cirrhosis. Indeed, hepatic cirrhosis has a high mortality rate, as currently available therapeutic options have significant side effects and are not generally efficacious in slowing or halting the progression of the fibrosis. Furthermore, many other types of extracellular matrix components are deposited during the pathogenesis of hepatic fibrosis, including at least five types of collagen, in particular collagen types I, III, and IV, as well as other matrix proteins [L. Ala-Kokko, *Biochem. J*, 244:75–9, 1987]. Thus, merely inhibiting synthesis of collagen type I would not necessarily slow or halt the development of hepatic fibrosis.

Thus, simply administering known in vitro inhibitors of collagen synthesis, deposition and cross-linking in an attempt to treat hepatic cirrhosis is ineffective. Clearly, new treatments for this incurable disease are required which specifically slow or halt the pathogenesis of fibrosis, without non-specific or toxic side effects.

There is thus a widely recognized need for, and it would be highly advantageous to have, a treatment for liver cirrhosis and fibrosis which inhibits fibrogenesis substantially without undesirable non-specific or toxic side effects.

SUMMARY OF THE INVENTION

Unexpectedly, it has been found, as described in the examples below, that Halofuginone can also inhibit the pathophysiological process of hepatic fibrosis in vivo, possibly by inhibiting collagen type I synthesis, although another mechanism or mechanisms could also be responsible. While inhibition of collagen type I synthesis is proposed as a plausible mechanism, it is not desired to be limited to a single mechanism, nor is it necessary since the in vivo data presented below clearly demonstrate the efficacy of Halofuginone as an inhibitor of hepatic fibrosis in vivo.

According to the teachings of the present invention, there is provided a method for the treatment of hepatic cirrhosis in a subject, comprising the step of administering to the subject a pharmaceutically effective amount of a compound having a formula:

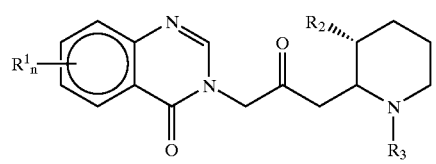

wherein:
$R_1$ is a member of the group consisting of hydrogen, halogen, nitro, benzo, lower alkyl, phenyl, and lower alkoxy;
$R_2$ is a member of the group consisting of hydroxy, acetoxy and lower alkoxy, and
$R_3$ is a member of the group consisting of hydrogen and lower alkenoxy-carbonyl;
wherein n is 1 or 2; and pharmaceutically acceptable salts thereof.

Preferably, the hepatic cirrhosis is caused by contact with a hepatotoxic chemical substance.

According to another embodiment of the present invention, there is provided a method for the treatment of hepatic fibrosis in a subject, the hepatic fibrosis being caused by contact with a hepatotoxic chemical substance, the method comprising the step of administering to the subject a pharmaceutically effective amount of a compound having a formula:

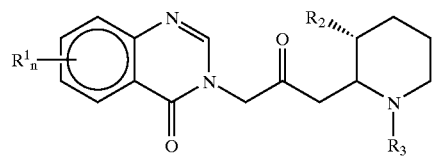

wherein:
$R_1$ is a member of the group consisting of hydrogen, halogen, nitro, benzo, lower alkyl, phenyl, and lower alkoxy;
$R_2$ is a member of the group consisting of hydroxy, acetoxy and lower alkoxy, and
$R_3$ is a member of the group consisting of hydrogen and lower alkenoxy-carbonyl;
wherein n is 1 or 2; and pharmaceutically acceptable salts thereof.

According to preferred embodiments of the present invention, the hepatic fibrosis is caused by a factor selected from the group consisting of chronic alcoholism, malnutrition, hemochromatosis, passive congestion, hypercholesterolemia, exposure to poisons or toxins, exposure to drugs, immune reactions, genetically determined sensitivities to a certain substance and infections.

More preferably, the hepatic fibrosis is caused by a factor selected from the group consisting of viral hepatitis, syphilis and a parasitic infection.

Most preferably, said parasitic infection is selected from the group consisting of *Schistosomiasis mansoni* and *S. japonica*.

According to yet another embodiment of the present invention, there is provided a method for the treatment of an existing condition of hepatic cirrhosis in a subject, comprising the step of administering to the subject a pharmaceutically effective amount of a compound having a formula:

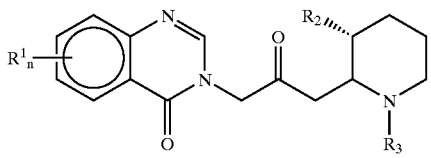

wherein:
$R_1$ is a member of the group consisting of hydrogen, halogen, nitro, benzo, lower alkyl, phenyl, and lower alkoxy;
$R_2$ is a member of the group consisting of hydroxy, acetoxy and lower alkoxy, and
$R_3$ is a member of the group consisting of hydrogen and lower alkenoxy-carbonyl;
wherein n is 1 or 2; and pharmaceutically acceptable salts thereof.

According to further preferred embodiments of the present invention, the compound is preferably Halofuginone. Hereinafter, the term "Halofuginone" is defined as a compound having a formula:

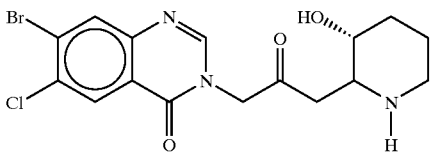

and pharmaceutically acceptable salts thereof. The composition preferably includes a pharmaceutically acceptable carrier for the compound.

According to another embodiment of the present invention, there is provided a method of manufacturing a medicament for treating hepatic cirrhosis, the hepatic cirrhosis being caused by contact with a hepatotoxic chemical substance, the method including the step of placing a pharmaceutically effective amount of a compound in a pharmaceutically acceptable carrier, the compound being a member of a group having a formula:

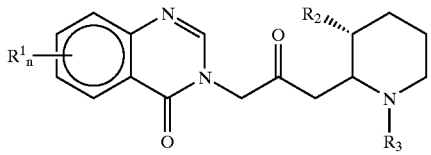

wherein:
$R_1$ is a member of the group consisting of hydrogen, halogen, nitro, benzo, lower alkyl, phenyl, and lower alkoxy; $R_2$ is a member of the group consisting of hydroxy, acetoxy, and lower alkoxy, and $R_3$ is a member of the group consisting of hydrogen and lower alkenoxy-carbonyl; wherein n is 1 or 2. Pharmaceutically acceptable salts thereof are also included.

According to yet another embodiment of the present invention, there is provided a composition for treating hepatic fibrosis, the hepatic fibrosis being caused by contact with a hepatotoxic chemical substance, the composition including a pharmaceutically effective amount of a compound in combination with a pharmaceutically acceptable carrier, the compound being a member of a group having a formula:

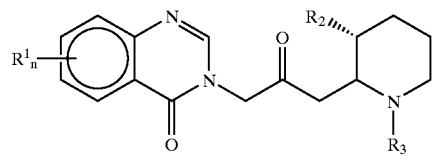

wherein:
$R_1$ is a member of the group consisting of hydrogen, halogen, nitro, benzo, lower alkyl, phenyl, and lower alkoxy; $R_2$ is a member of the group consisting of hydroxy, acetoxy, and lower alkoxy; and $R_3$ is a member of the group consisting of hydrogen and lower alkenoxy; wherein n is 1 or 2. Pharmaceutically acceptable salts thereof are also included.

According to the present invention, there is also provided a method of manufacturing a medicament for treating hepatic fibrosis, the hepatic fibrosis being caused by contact with a hepatotoxic chemical substance, the method including the step of placing a pharmaceutically effective amount of a compound in a pharmaceutically acceptable carrier, the compound being a member of a group having a formula:

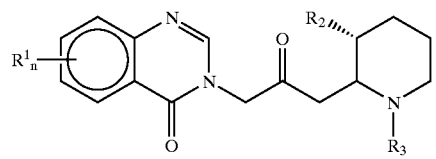

wherein:
$R_1$ is a member of the group consisting of hydrogen, halogen, nitro, benzo, lower alkyl, phenyl, and lower alkoxy; $R_2$ is a member of the group consisting of hydroxy, acetoxy, and lower alkoxy; and $R_3$ is a member of the group consisting of hydrogen and lower alkenoxy-carbonyl; wherein n is 1 or 2. Pharmaceutically acceptable salts thereof are also included.

According to still another embodiment of the present invention, there is provided a method for the treatment of hepatic cirrhosis in a subject, with the proviso that the hepatic cirrhosis is not caused by chronic alcoholism, viral hepatits or an autoimmune condition, the method comprising the step of administering to the subject a pharmaceutically effective amount of a compound having a formula:

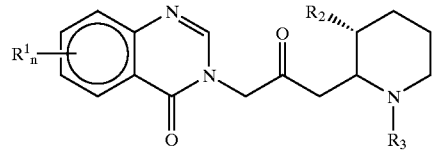

wherein:
$R_1$ is a member of the group consisting of hydrogen, halogen, nitro, benzo, lower alkyl, phenyl, and lower alkoxy; $R_2$ is a member of the group consisting of hydroxy, acetoxy and lower alkoxy, and $R_3$ is a member of the group consisting of hydrogen and lower alkenoxy-carbonyl; wherein n is 1 or 2; and pharmaceutically acceptable salts thereof.

According to yet another embodiment of the present invention, there is provided a method for the treatment of hepatic fibrosis in a subject, with the proviso that the hepatic fibrosis is not caused by chronic alcoholism, viral hepatitis or an autoimmune condition, the method comprising the step of administering to the subject a pharmaceutically effective amount of a compound having a formula:

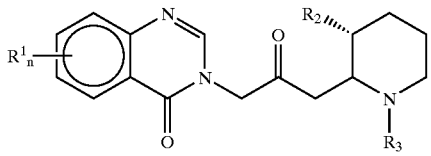

wherein:
$R_1$ is a member of the group consisting of hydrogen, halogen, nitro, benzo, lower alkyl, phenyl, and lower alkoxy; $R_2$ is a member of the group consisting of hydroxy, acetoxy and lower alkoxy, and $R_3$ is a member of the group consisting of hydrogen and lower alkenoxy-carbonyl; wherein n is 1 or 2; and pharmaceutically acceptable salts thereof.

Hereinafter, the term "subject" refers to the human or lower animal to whom Halofuginone was administered. The term "patient" refers to human subjects. The term "treatment" includes slowing or halting the progression of hepatic cirrhosis or fibrosis once it has arisen. The phrase "substantially preventing the genesis" of hepatic cirrhosis or fibrosis is understood to refer to the prevention of the appearance of clinical or preclinical symptoms of these conditions, including the prevention of those symptoms which are indirectly related to the fibrotic and cirrhotic processes themselves, such as hemorrhage from esophageal blood vessels.

Hereinafter, the term "hepatotoxic chemical substance" refers to chemicals which are not normally consumed or introduced into the circulation, and which have a harmful effect on the subject upon contact with the subject through introduction into the circulation of the subject, consumption by the subject or introduction to the subject through another route of administration.

Although the specific quinazolinone derivative "Halofuginone" is referred to throughout the specification, it is understood that other quinazolinone derivatives may be used in its place, these derivatives having the formula:

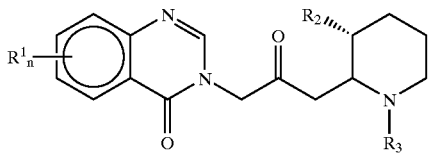

wherein:
$R_1$ is a member of the group consisting of hydrogen, halogen, nitro, benzo, lower alkyl, phenyl and lower alkoxy; $R_2$ is a member of the group consisting of hydroxy, acetoxy and lower alkoxy, and $R_3$ is a member of the group consisting of hydrogen and lower alkenoxy-carbonyl; wherein n is 1 or 2. Pharmaceutically acceptable salts thereof are also included.

While the invention will now be described in connection with certain preferred embodiments in the following figures and examples so that aspects thereof may be more fully understood and appreciated, it is not intended to limit the invention to these particular embodiments. On the contrary, it is intended to cover all alternatives, modifications and equivalents as may be included within the scope of the invention as defined by the appended claims. Thus, the following figures and examples which include preferred embodiments will serve to illustrate the practice of this invention, it being understood that the particulars shown are by way of example and for purposes of illustrative discussion of preferred embodiments of the present invention only, and are presented in the cause of providing what is believed to be the most useful and readily understood description of formulation procedures as well as of the principles and conceptual aspects of the invention.

BRIEF DESCRIPTION OF THE DRAWINGS

The invention is herein described, by way of example only, with reference to the accompanying drawings, wherein.

DESCRIPTION OF THE PREFERRED EMBODIMENTS

Figure 1A:
FIGS. 1A–1D illustrate the effect of Halofuginone on collagen α1(I) gene expression in rat liver.
Figure 1B:
Figure 1C:
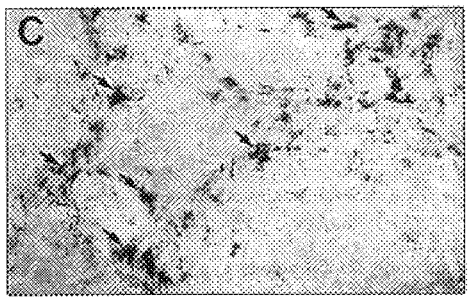
Figure 1D:
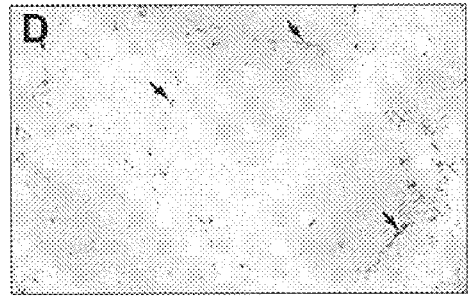

Unexpectedly, it has been found, as described in the examples below, that Halofuginone can inhibit the pathological process of hepatic cirrhosis in vivo, possibly by inhibiting collagen type I synthesis, although another mechanism or mechanisms could also be responsible. Indeed, irrespective of the specific mechanism, the data presented below clearly demonstrate the efficacy of Halofuginone in vivo for inhibition of the pathological progression of hepatic fibrosis.

Such a finding is unexpected for three reasons. First, the behavior of Halofuginone in vitro does not exactly correspond to its behavior in vivo. This can be demonstrated by the differential effect of Halofuginone observed with bone chondrocytes in vivo and in vitro. Halofuginone inhibits the synthesis of collagen type I in chrondrocytes in vitro, as demonstrated in U.S. Pat. No. 5,449,678. However, chickens treated with Halofuginone were not reported to have an increased rate of bone breakage, indicating that the effect is not seen in vivo. Thus, the exact behavior of Halofuginone in vivo cannot always be accurately predicted from in vitro studies.

Second, other inhibitors of collagen synthesis, deposition and cross-linking have not proved effective for the treatment of hepatic cirrhosis, demonstrating that inhibition of collagen production alone is not sufficient for determining the success or failure of a treatment for hepatic fibrosis. Thus, the finding that Halofuginone can successfully inhibit hepatic fibrosis in vivo is both novel and non-obvious.

Third, Halofuginone has only been shown to be a collagen type I inhibitor. However, the formation of fibrotic tissue in the liver is characterized by the deposition of abnormally large amounts of extracellular matrix components, including at least five types of collagen, in particular collagen types I, III, and IV, as well as other matrix proteins [L. Ala-Kokko, Biochem. J, 244:75–9, 1987]. Thus, the ability of Halofuginone to inhibit collagen type I synthesis and deposition cannot predict the ability of Halofuginone to slow, reduce or other ameliorate the pathogenesis of hepatic fibrosis.

Finally, all other prior art references have only taught the efficacy of Halofuginone on cells such as fibroblasts. In the liver, Ito cells have been shown to be the source of the extracellular matrix components which are produced during liver fibrosis, so this cell type is crucial to the pathogenesis of liver fibrosis [S. L. Friedman, New Eng. J. Med., 328:1828–35, 1993]. However, Ito cells are a completely different cell type than fibroblasts. In addition, Halofuginone has been shown to be surprisingly effective for the prevention of the abnormal expression of smooth muscle cell characteristics of stellate cells, which are certainly different from those cells previously shown to be involved in fibrotic processes. Even if the behavior of Halofuginone on cells of a certain type could be predicted, such a prediction would certainly not be reliable for cells outside of that type. Thus, the effect of Halofuginone on Ito cells is not predictable from its effect on fibroblasts.

Thus, nothing in the prior art taught that Halofuginone would be useful in the treatment of hepatic fibrosis in vivo. Furthermore, the ability of Halofuginone, and related compounds, to slow or halt progression of fibrosis in the liver is both novel and non-obvious. The demonstration of such an ability in vivo is particularly unexpected, given the differential responses seen in vitro and in vivo to Halofuginone. Furthermore, the ability of Halofuginone to treat and ameliorate an existing liver cirrhotic condition, as demonstrated below, is particularly unexpected, since previously Halofuginone was shown to have greater efficacy for the prevention of liver cirrhosis through prophylactic administration.

The present invention may be more readily understood with reference to the following illustrative examples and figures. It should be noted that although reference is made exclusively to Halofuginone, it is believed that the other quinazolinone derivatives described and claimed in U.S. Pat. No. 3,320,124, the teachings of which are incorporated herein by reference, have similar properties.

The present invention is of a treatment for hepatic cirrhosis and fibrosis with quinazolinone-containing compounds such as Halofuginone. Both compositions with specific pharmaceutical formulations and methods of using these compounds are described below.

Although the pathogenesis of hepatic cirrhosis is not fully understood, animal models for the disease have been successfully developed. Hepatic fibrosis has been induced in rats by the intraperitoneal injection of dimethylnitrosamine, with a relatively short onset of action: within three weeks of administration of dimethylnitrosamine to rats, hepatic fibrosis was already evident [A. M. Jezequel et al., J. Hepatol., 5:174–81, 1987].

Dimethylnitrosamine-induced hepatic fibrosis is characterized by increased deposition of extracellular matrix components, including various types of collagen such as collagen type I. Thus, inhibition of fibrosis, as in both dimethylnitrosamine-induced and other types of hepatic fibrosis, depends upon the slowing or halting of the pathological process leading to the production of fibrotic tissue.

Therefore, compounds which are intended for the inhibition of hepatic cirrhosis must be tested in an in vivo model, such as the dimethylnitrosamine model described above, for their ability to slow or halt the pathological process leading to deposition of fibrotic tissue. Such experiments were conducted for the collagen type I synthesis inhibitor Halofuginone, as described in greater detail in Examples 1 and 2 below.

Furthermore, once demonstrably effective compounds have been discovered, specific formulations and routes of administration must be elucidated for maximum efficacy of the treatment. Such formulations and routes of administration must enable the compound to be effectively absorbed and delivered to the desired site of treatment, while minimizing non-specific side effects caused by systemic distribution of the compound. Illustrative examples of these formulations and routes of administration for quinazolinone-containing compounds such as Halofuginone are given in Examples 3–5 below.

EXAMPLE 1

Effect of Halofuginone on Histology and Morphology of Rat Liver

Histological examination of liver samples from control and dimethylnitrosamine-treated rats revealed that dimethylnitrosamine induced specific morphological changes in rat liver, including increased collagen fiber content. Dimethylnitrosamine is an example of a hepatotoxic chemical substance as previously defined. Halofuginone substantially inhibited the occurrence of these morphological changes, resulting in rat liver of more normal appearance.

The experimental method was as follows. Male Sprague-Dawley rats were divided into four groups. Two groups were injected intraperitoneally with 1% dimethylnitrosamine in saline for three consecutive days per week for 3 weeks, at a dose of 1 ml/kg body weight. This dosage regimen will induce severe liver fibrosis. The other two groups of rats, control rats, were injected with saline. One group of dimethylnitrosamine-treated rats and one control group were fed Halofuginone in the diet at a dose of 5 mg/kg weight of diet, starting three days before the dimethylnitrosamine injections were administered. At the end of the experimental period, the rats were sacrificed and the liver was removed and weighed.

Liver samples were taken for histological examination. Briefly, the tissue samples were collected into phosphate-buffered saline (PBS) and fixed overnight in 4% paraformaldehyde in PBS at 4° C. Serial 5 $\mu$m sections were prepared after the samples had been dehydrated in graded ethanol solutions, cleared in chloroform and embedded in Paraplast. Differential staining of collagenous and non-collagenous proteins was performed with 0.1% Sirius red and 0.1% fast green as a counter-stain in picric acid. This procedure stains collagen red [Gascon-Barre, M., et al., J. Histochem. Cytochem., 37:377–381, 1989].

Liver samples were then hybridized with a probe for rat collagen $\alpha1(I)$ expression. For hybridization with the genetic probe, the sections were deparafinized in xylene, rehydrated through a graded series of ethanol solutions, rinsed in distilled water for 5 minutes and then incubated in 2×SSC at 70° C. for 30 minutes. The sections were then rinsed in distilled water and treated with pronase, 0.125 mg/ml in 50 mM Tris-HCl, 5 mM EDTA, pH 7.5, for 10 minutes. After digestion, the slides were rinsed with distilled water, post-fixed in 10% formalin in PBS and blocked in 0.2% glycine. After blocking, the slides were rinsed in distilled water, rapidly dehydrated through graded ethanol solutions and air-dried for several hours. Before hybridization, the 1600 bp rat collagen α1(I) insert was cut out from the original plasmid, pUC18, and inserted into the pSafyre plasmid. The sections were then hybridized with this probe after digoxigenin-labeling [M. Pines et al., *Matrix Biology*, 14:765–71, 1996].

FIG. 1 shows in situ hybridization of a section of rat liver tissue with rat collagen α1(I) probe. A low expression of collagen α1(I) gene is seen in liver of control rats (FIG. 1A) or rats given Halofuginone alone (FIG. 1B). A marked increase in the expression of collagen α1(I) gene was seen in the liver of rats given dimethylnitrosamine alone (FIG. 1C). The gene expression was mainly in the septa surrounding the lobules at the site of sparse collagenous tissue. Rats given both Halofuginone and dimethylnitrosamine show a marked reduction in the expression of collagen α1(I) gene (FIG. 1D), as compared to rats given dimethylnitrosamine alone. Although this dose of Halofuginone substantially reduced the increase in rat collagen α1(I) gene expression caused by dimethylnitrosamine, it did not completely inhibit such expression as traces can be observed (see arrows). However, the substantially reduced rat collagen α1(I) gene expression indicates that Halofuginone is effective against the pathological induction of expression by dimethylnitrosamine.

Sections of rat liver tissue were stained with Sirius red to demonstrate collagen content of the tissue, although results are not shown pictorially since the histological samples must be viewed in color in order to see the effects. Almost no collagen fibers were observed in liver tissue taken from control rats or rats given Halofuginone alone. The livers of the dimethylnitrosamine-treated rats exhibited an increase in collagen content, displaying bundles of collagen surrounding the lobules, resulting in large fibrous septa. The thickening of these collagen bundles was markedly reduced in rats given both dimethylnitrosamine and Halofuginone, again indicating the ability of Halofuginone to substantially inhibit the pathophysiological process of fibrosis induced by dimethylnitrosamine.

Interestingly, the relatively high dose of dimethylnitrosamine caused such severe hepatic fibrosis that four out of the six dimethylnitrosamine-treated rats which were not given Halofuginone had died by the end of three weeks. By contrast, only one of the six rats given both dimethylnitrosamine and Halofuginone died. Each of the six rats in the two groups which were not given dimethylnitrosamine survived. Thus, Halofuginone alone had no toxicity, yet was able to almost completely prevent dimethylnitrosamine-induced death.

Dimethylnitrosamine-induced changes on the gross morphological level were also inhibited by Halofuginone. Rats treated with dimethylnitrosamine alone had significantly lower liver weights (4.5 g and 5.0 g), particularly when compared to control rats and rats given Halofuginone alone (12±1 g and 11±1.5 g, respectively). Rats given both Halofuginone and dimethylnitrosamine had liver weights (8.5±1.7 g) that were almost twice that of rats given dimethylnitrosamine alone, although somewhat reduced as compared to control rats.

Thus, Halofuginone was able to prevent the appearance of the effects of dimethylnitrosamine-induced fibrosis on all levels: near-elimination of dimethylnitrosamine-induced fatalities, and marked reduction of gross and fine morphological changes caused by dimethylnitrosamine-induced fibrosis. Clearly, the effects of Halofuginone are both potent and specific for the prevention of the morphological changes produced during the pathological process of hepatic fibrosis.

EXAMPLE 2

Effect of Halofuginone on Mild Fibrosis in Rat Liver

Halofuginone substantially completely prevented mild dimethylnitrosamine-induced fibrosis, as demonstrated by the measurement of collagen α1(I) gene expression and hydroxyproline content. The specific experimental method used was similar to that of Example 1, except that the dimethylnitrosamine-treated rats were only given 0.25% dimethylnitrosamine in saline, a much lower dose than that given in Example 1 above. Also, the duration of treatment was longer before the rats were sacrificed: 4 weeks as opposed to 3 weeks in Example 1.

The expression of the collagen α1(I) gene was measured as described in Example 1 above. For hydroxyproline analysis, liver samples were hydrolyzed for 22 hours at 110° C. with 6 N HCl. Nitrogen was determined after Kjeldahl digestion by the spectrophotometric procedure using an autoanalyzer as described by Krom [M. D. Krom, *Analyst*, 105:305–16, 1980]. The collagen-unique amino acid hydroxyproline from the same hydrolysate was determined by amino acid analysis (Biotronik LC 5000, Germany) after post-column derivatization on a cation exchange column (BTC 2710, Biotronik). The results are expressed as the percentage of collagen in total liver proteins.

Figure 2:
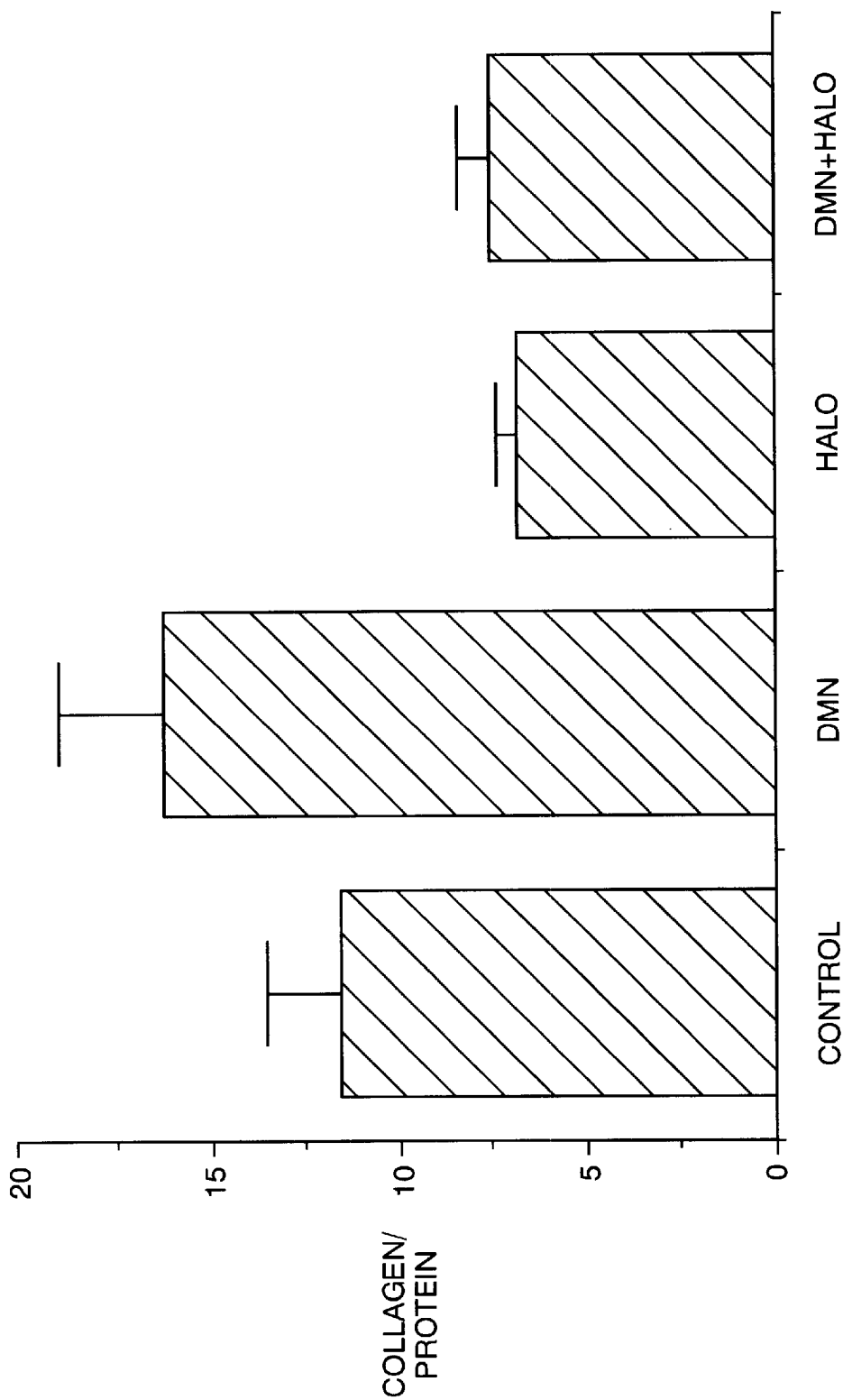
FIG. 2 illustrates the effect of Halofuginone on hydroxyproline concentration in rat liver.

Hydroxyproline is an amino acid which is present in relatively large amounts in collagen, and therefore serves as an indicator for the overall level of collagen in a particular tissue. Thus, as shown in FIG. 2, dimethylnitrosamine clearly caused a significant increase in hydroxyproline concentration, and therefore of collagen levels, in the livers of rats. This increase was completely inhibited by treatment with Halofuginone. However, administration of Halofuginone to rats which were not given dimethylnitrosamine did not cause any change in hydroxyproline concentration. Therefore, the effect of Halofuginone was simply to inhibit the dimethylnitrosamine-induced increase in hydroxyproline concentration.

Figure 3A:
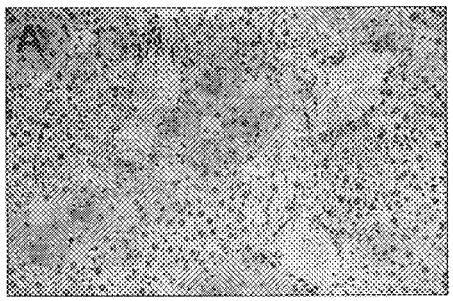
FIGS. 3A–3D illustrate the effect of Halofuginone on moderate fibrosis in rat liver.
Figure 3B:
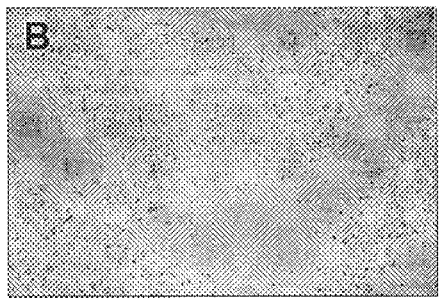
Figure 3C:
Figure 3D:
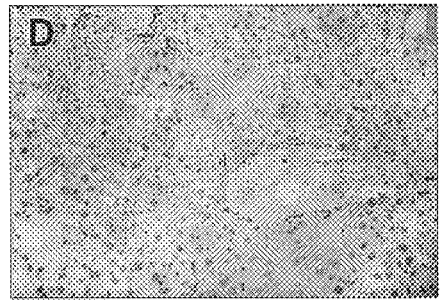

FIG. 3C demonstrates that such a low dose of dimethylnitrosamine still caused an increase in collagen α1(I) gene expression, especially by cells surrounding the blood vessels. FIG. 3D shows that this increased gene expression was abolished by Halofuginone. Again, as in Example 1 above, Halofuginone alone had no effect on collagen α1(I) gene expression (FIG. 3B), while control rats also had no collagen α1(I) gene expression (FIG. 3A).

Thus, clearly Halofuginone completely inhibited the increased levels of collagen synthesis induced by dimethylnitrosamine in the livers of rats. However, Halofuginone alone did not demonstrate any such effect in rats, indicating that the effect of Halofuginone is specific for inhibition of those pathophysiological processes, such as collagen synthesis, which are caused by dimethylnitrosamine-induced fibrosis. Furthermore, Halofuginone was clearly able to substantially completely abrogate the biochemical and physiological changes caused by dimethylnitrosamine, as demonstrated by both Examples 1 and 2.

EXAMPLE 3

Inhibition of Fibrosis Induced by Bile Duct Ligation

In addition to dimethylnitrosamine-induced liver fibrosis, a second model of liver fibrosis in rats is available. This model relies upon surgical ligation of the bile duct to induce liver fibrosis, rather than requiring the administration of exogeneous substances or toxic chemicals, and has been shown to be a suitable model for studying human liver cirrhosis [Kountaras, J. et al., *Br. J. Exp. Pathol.*, 65:305–311, 1984; Muriel, P. et al., *J. Hepatol.*, 21:95–102, 1994; Muriel P. et al., *J. Appl. Tox.*, 15:449–453, 1995]. Thus, the particular advantage of the bile duct ligation model is that any protective treatments must directly protect the liver from the pathological changes induced by fibrosis, rather than indirectly altering the effects of the exogeneous substance which is used to cause liver fibrosis in the animal model. The experimental method was as follows.

Male Wistar rats, weighing 200–250 g, were divided into four experimental groups with 3 rats in each group. The first group did not have bile duct ligation surgery and was not given Halofuginone. The second group did not have bile duct ligation surgery and was given Halofuginone. It should be noted that all animals in the first two groups underwent sham operations which included all steps of the actual surgical procedure, with the exception of the bile duct ligation itself. The third group had bile duct ligation surgery and was not given Halofuginone. The fourth group had bile duct ligation surgery and was given Halofuginone. The actual surgical procedure was essentially similar to that reported in the literature [Kountaras, J. et al., *Br. J. Exp. Pathol.*, 65:305–311, 1984].

All animals were given drinking water ad libitum. Rats which were given Halofuginone were fed Halofuginone in the normal rat diet at a concentration of 5 mg per kg diet weight for one week before surgery and for the duration of the experimental period, which was either 3 or 7 days after the surgical operation. Rats were sacrificed at the end of the experimental period. Both collagen content (through Sirius red staining) and collagen $\alpha 1(I)$ gene expression were measured as described above in Example 1. In addition, serum alkaline phosphatase, alanine aminotransferase and aspartate aminotransferase levels were measured calorimetrically by a Hitachi Auto-analyzer System of Boerringher-Mannheim. Results are as follows.

No collagen synthesis was observed in rats which underwent a sham operation. Furthermore, these rats did not show any increase in body weight or liver weight, or any altered liver histology. Finally, these rats did not show any changes in the levels of the enzymes alkaline phosphatase, alanine aminotransferase or aspartate aminotransferase either 3 or 7 days after the operation, regardless of whether Halofuginone was administered.

By contrast, elevated levels of all three enzymes were observed in rats which underwent bile duct ligation in both the Halofuginone-treated and untreated groups. These elevated levels are characteristic markers for the pathological process of liver fibrosis and cirrhosis. However, rats which were fed Halofuginone had lower levels of these enzymes than rats which were not. Specifically, rats which were not given Halofuginone had 56% higher alanine aminotransferase, 257% alkaline phosphatase and 15% higher aspartate aminotransferase levels than rats which were fed Halofuginone. Thus, clearly Halofuginone reduced the extent of elevated enzyme levels in rats which underwent bile duct ligation.

Furthermore, Halofuginone significantly reduced the bile duct ligation-induced increased in collagen synthesis and collagen $\alpha 1(I)$ gene expression, when rats which underwent bile duct ligation and which were fed Halofuginone were compared to rats which only underwent bile duct ligation.

Thus, Halofuginone clearly was able to inhibit the process of liver fibrosis in the model of bile duct ligation-induced fibrosis in rats.

EXAMPLE 4

Treatment of Liver Cirrhosis by Halofuginone

Another model of liver cirrhosis is the chemical induction of such cirrhosis with thioacetamide (TAA) in rats. The administration of thioacetamide by intraperitoneal (i.p.) injection induces liver cirrhosis, including the deposition of fibrotic tissues and the loss of liver function. Halofuginone was shown to be effective for both the treatment of liver cirrhosis after the appearance of cirrhotic symptoms, and for the prevention of liver cirrhosis. The latter effect is particularly surprising since previous medicaments had not been previously shown to be able to treat an existing cirrhotic condition, which is important since the administration of such medicaments to human patients is typically performed only after liver cirrhosis has arisen in the patient. The experimental method was as follows.

Male Sprague-Dawley rats were divided into three groups. Two groups were injected intraperitoneally with TAA twice weekly for 12 weeks, at a dose of 200 mg/kg body (Muller, A. et al., *Exp. Pathol.*, 34:229–236, 1988; Hori, N. et al., *Dig. Dis. Sci.*, 38:2195–2202, 1993). Such long term administration of TAA results in characteristic lesions which demonstrate cirrhosis-like patterns of micronodular cirrhosis in the liver of the rats. The other group of rats, control rats, was injected with saline. One group of TAA-treated rats and one control group were fed Halofuginone in the diet at a dose of 5 ppm. Two separate experiments were performed, one experiment for demonstrating the efficacy of Halofuginone for the treatment of liver cirrhosis, and one experiment for demonstrating the prevention of liver cirrhosis. Again, it should be emphasized that previously only the efficacy of prevention of liver cirrhosis with Halofuginone had been demonstrated, but not the treatment of existing liver cirrhosis.

Prevention of Liver Cirrhosis

For this experiment, rats in group 1 received only Halofuginone (n=4); rats in group 2 received TAA alone without Halofuginone (n=6); and rats in group 3 received TAA with Halofuginone (n=6). Groups 1and 3 received Halofuginone starting three days before the TAA injections were administered. At the end of the experimental period, the rats were sacrificed and the liver was removed and weighed.

Liver samples were taken for histological examination. Briefly, the tissue samples were collected into phosphate-buffered saline (PBS) and fixed overnight in 4% paraformaldehyde in PBS at 4° C. Serial 5 $\mu$m sections were prepared after the samples had been dehydrated in graded ethanol solutions, cleared in chloroform and embedded in Paraplast. Differential staining of collagenous and non-collagenous proteins was performed with 0.1% Sirius red and 0.1% fast green as a counter-stain in picric acid. This procedure stains collagen red [Gascon-Barre, M., et al., *J. Histochem. Cytochem.*, 37:377–381, 1989].

In addition, the livers were scored in a double-blind evaluation, on a scale of 0–4, for the appearance of fibrotic tissue. Previously, an excellent correlation has been demonstrated between such manual double-blind scores and the deposition of collagen as evaluated by histology, for example.

Figure 4A:
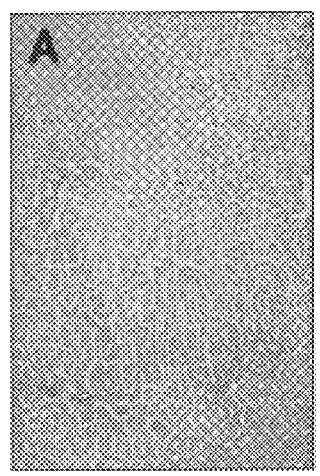
FIGS. 4A–4F illustrate the effect of Halofuginone for the prevention of TAA-induced liver cirrhosis.
Figure 4B:
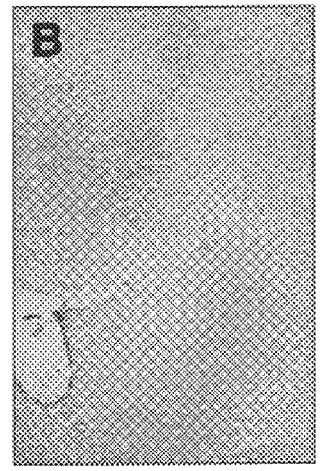
Figure 4C:
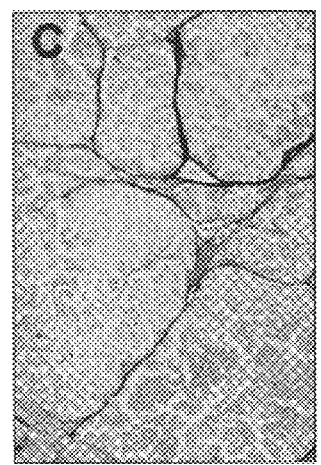
Figure 4D:
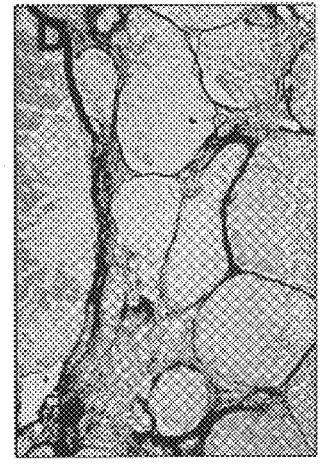
Figure 4E:
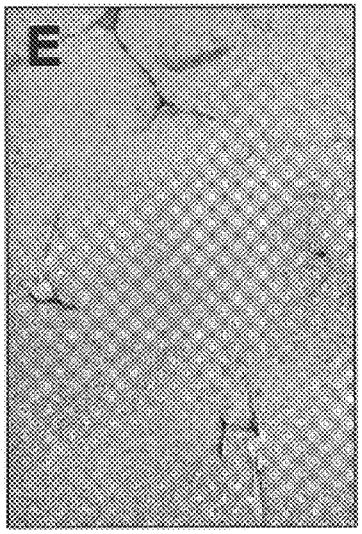
Figure 4F:
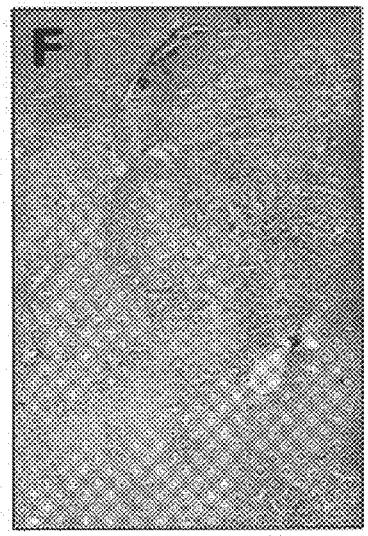
Figure 5A:
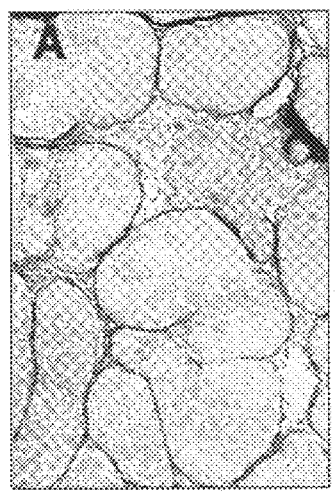
FIGS. 5A–5F illustrate the effect of Halofuginone for the treatment of TAA-induced liver cirrhosis.
Figure 5B:
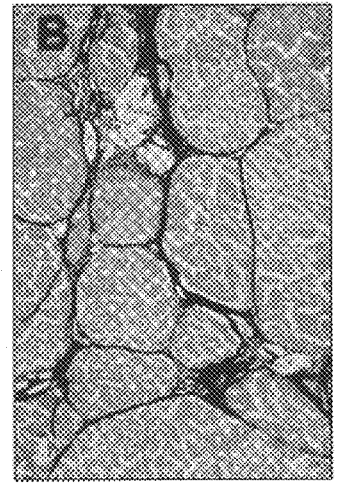
Figure 5C:
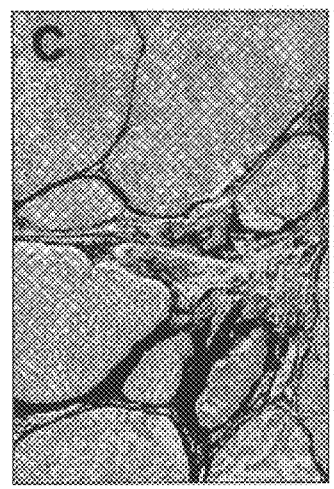
Figure 5D:
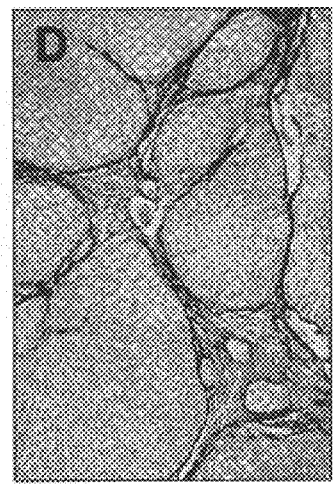
Figure 5E:
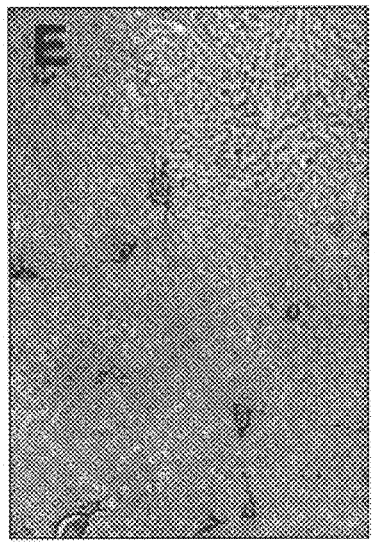
Figure 5F:
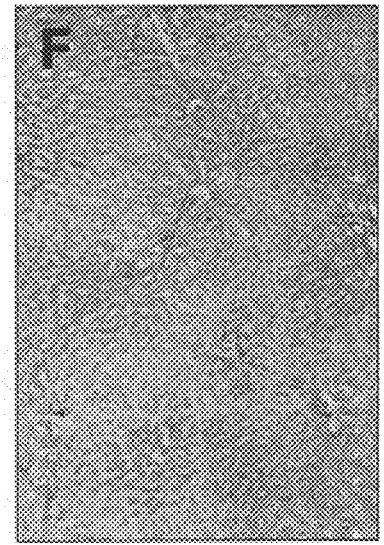

Sections of rat liver tissue were stained with Sirius red to demonstrate collagen content of the tissue, as shown in FIGS. 4A–4F. Almost no collagen fibers were observed in liver tissue taken from rats given Halofuginone alone (FIGS. 4A and 4B, representing samples from two different rats). The livers of the TAA-treated rats exhibited an increase in collagen content, displaying bundles of collagen surrounding the lobules, resulting in large fibrous septa (FIGS. 4C and 4D, representing samples from two different rats). The thickening of these collagen bundles was markedly reduced in rats given both TAA and Halofuginone, again indicating the ability of Halofuginone to substantially inhibit the pathophysiological process of fibrosis induced by TAA (FIGS. 4E and 4F, representing samples from two different rats).

TAA-induced changes on the gross morphological level were also inhibited by Halofuginone, as shown by the manual double blind scores. Rats treated with TAA alone had an average score of 2.16±0.7, while control rats had a score of 0 and rats given both Halofuginone and TAA had an average score of 1.25±0.8, which is significantly lower than the average score of rats given TAA alone. Thus, no effect of Halofuginone on body weight or spleen weight was demonstrated (data not shown), while the fibrotic scores for liver were reduced by 43%.

Thus, Halofuginone was able to prevent the appearance of the effects of TAA-induced fibrosis on all levels, including marked reduction of gross and fine morphological changes caused by TAA-induced fibrosis.

Treatment of Liver Cirrhosis

The experimental method was similar for the treatment of existing liver cirrhosis, as previously described, except that Halofuginone was not administered until after the induction of liver cirrhosis by treatment with TAA for twelve weeks. For this experiment, rats in group 1 received only TAA (n=6) and were killed after the initial twelve week period. The remaining rats were divided into two groups, and either received no further treatment (group 2, n=8), or Halofuginone (group 3, n=8). Rats in groups 2 and 3 were killed four weeks later.

As previously described, sections of rat liver tissue were stained with Sirius red to demonstrate collagen content of the tissue, as shown in FIGS. 5A–5F. The livers of the TAA-treated rats exhibited an increase in collagen content, displaying bundles of collagen surrounding the lobules, resulting in large fibrous septa (FIGS. 4A and 4B, and 4C and 4D, representing samples from four different rats). The thickening of these collagen bundles was markedly reduced in rats given both TAA and Halofuginone, again indicating the ability of Halofuginone to substantially inhibit the pathophysiological process of fibrosis induced by TAA (FIGS. 4E and 4F, representing samples from two different rats).

TAA-induced changes on the gross morphological level were also inhibited by Halofuginone, as shown by the manual double blind scores. Rats treated with TAA alone had an average score of 2.16±0.7 or 3.06±1.7 for groups 1 and 2 respectively, while rats given both Halofuginone and TAA had an average score of 1.18±1.6 for group 3, which is significantly lower than the average score of rats given TAA alone and is similar to the effect of Halofuginone as a prophylactic agent. Thus, the fibrotic scores for liver were significantly reduced, even to as great an extent as for rats given Halofuginone before TAA was administered, thereby demonstrating the efficacy of Halofuginone for the treatment of an existing liver cirrhotic and fibrotic condition.

Clearly, the effects of Halofuginone are both potent and specific for the prevention of the morphological changes produced during the pathological process of hepatic fibrosis, both as a treatment for existing fibrotic and cirrhotic conditions, and as a preventative agent.

EXAMPLE 5

Effect of Halofuginone on Stellate Cells

Liver cirrhosis was induced with TAA as previously described. The types of cells injured through the cirrhotic process were then examined, and stellate cells of the liver were found to be targets of the TAA-induced liver cirrhosis. Previously, stellate cells had been shown to produce the excess extracellular matrix components associated with liver cirrhosis and fibrosis (S. L. Friedman, *New England J. Med.,* 328:1828–1835, 1993). These cells are located in the subendothelial space, between the apical membrane of hepatocytes and the ablumenal side of the sinusoidal endothelial cells. The intimate association between the stellate cells and the neighboring cell types facilitates intercellular transport and paracrine stimulation by soluble mediators. In injured liver, these cells acquire features of myofibroblasts and express smooth muscle cytoskeletal markers such as smooth muscle actin. The level of smooth muscle actin is greatly increased during liver injury in regions of fibrous septa formation adjacent to hepatocellular injury, and is localized within the microfilament bundles of cells. In the present experiments, Halofuginone was shown to ameliorate the effect of TAA-induced damage to the stellate cells. The experimental method was as follows.

Rats were treated with TAA alone or TAA with Halofuginone as previously described in Example 4 for the use of Halofuginone as both a prophylactic treatment and a treatment for existing liver cirrhosis. Tissue samples were also prepared as previously described, except that rather than undergoing staining for collagen, the samples were incubated with smooth muscle actin antibodies in a 1:1000 dilution, with detection performed by the Histomouse SP kit according to the instructions of the manufacturer (Zymed Laboratories Inc., San Francisco, Calif., USA).

Figure 6A:
FIGS. 6A–6C illustrate the effect of Halofuginone on stellate cells when administered prophylactically for the prevention of TAA-induced liver cirrhosis.
Figure 6B:
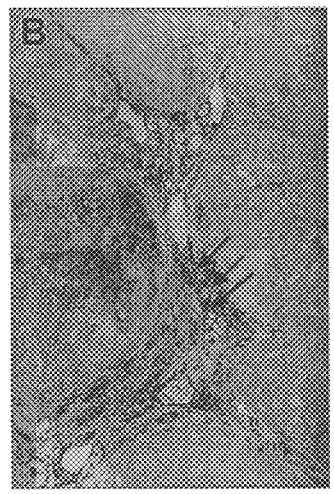
Figure 6C:
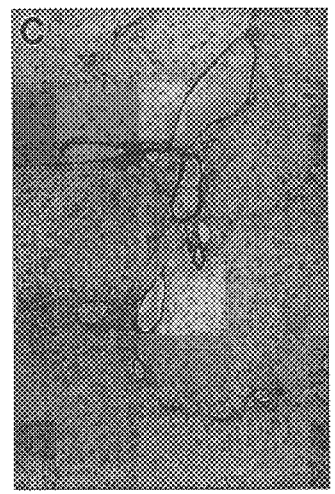
Figure 7A:
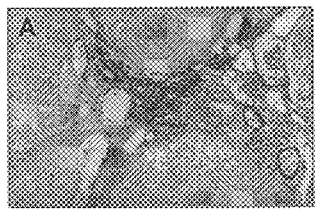
FIGS. 7A–7C illustrate the effect of Halofuginone on stellate cells for the treatment of TAA-induced liver cirrhosis.

FIG. 6 shows the detection of smooth muscle actin in liver tissue taken from rats in the prevention experiment, while FIG. 7 shows such detection in liver tissue taken from rats in the treatment experiment. As shown in FIG. 6A, in samples of liver tissue taken from control rats, smooth muscle actin was only found in cells surrounding the blood vessels, which is the normal pattern of detection. However, samples of liver taken from rats after the administration of TAA alone show that TAA-induced liver cirrhosis causes smooth muscle actin to also be expressed by stellate cells, found in the septa formed by the deposition of additional extracellular matrix components (FIG. 6B). Such abnormal, pathological expression of smooth muscle actin was prevented by the prophylactic administration of Halofuginone (FIG. 6C).

Figure 7B:
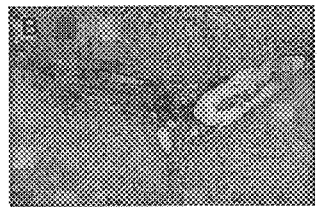
Figure 7C:
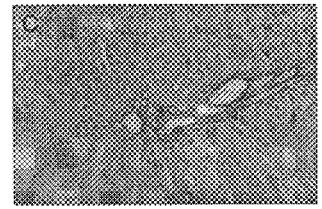

Similarly, the administration of TAA alone in the second experiment, testing Halofuginone as a treatment of existing liver cirrhosis, also resulted in a high level of smooth muscle actin expression by stellate cells (FIG. 7A), which was maintained 8 weeks later (FIG. 7B). However, the administration of Halofuginone, even after the induction of liver cirrhosis, significantly reduced the pathological expression of smooth muscle actin (FIG. 7C). Thus, again Halofuginone is shown to be effective as both a prophylactic agent for preventing liver cirrhosis, and for the treatment of existing cirrhosis, at least partially in the liver by preventing the pathological expression of smooth muscle characteristics by stellate cells.

EXAMPLE 6

Suitable Formulations for Administration of Halofuginone

Halofuginone can be administered to a subject in a number of ways, which are well known in the art. Hereinafter, the term "subject" refers to the human or lower animal to whom Halofuginone was administered. For example, administration may be done orally, or parenterally, for example by intravenous drip or intraperitoneal, subcutaneous, or intramuscular injection.

Compositions for oral administration include powders or granules, suspensions or solutions in water or non-aqueous media, sachets, capsules or tablets. Thickeners, diluents, flavorings, dispersing aids, emulsifiers or binders may be desirable.

Formulations for parenteral administration may include but are not limited to sterile aqueous solutions which may also contain buffers, diluents and other suitable additives.

According to a preferred embodiment of the present invention, one additional route of administration of Halofuginone is through a medical device.

Dosing is dependent on the severity of the symptoms and on the responsiveness of the subject to Halofuginone. Persons of ordinary skill in the art can easily determine optimum dosages, dosing methodologies and repetition rates.

EXAMPLE 7

Method of Treatment of Hepatic Fibrosis and Cirrhosis

As noted above, Halofuginone has been shown to be an effective inhibitor of hepatic fibrosis, a precursor of hepatic cirrhosis. The following example is an illustration only of a method of treating hepatic fibrosis and cirrhosis with Halofuginone, and is not intended to be limiting.

The method includes the step of administering Halofuginone, in a pharmaceutically acceptable carrier as described in Example 4 above, to a subject to be treated. Halofuginone is administered according to an effective dosing methodology, preferably until a predefined endpoint is reached, such as the absence of further progression of hepatic fibrosis or cirrhosis in the subject, the inhibition of hepatic fibrosis or cirrhosis or the prevention of the formation of hepatic fibrosis or cirrhosis.

Examples of types of hepatic fibrosis for which such a treatment would be effective include, but are not limited to, hepatic fibrosis caused by chronic alcoholism, malnutrition, hemochromatosis, passive congestion, hypercholesterolemia, exposure to poisons or toxins, exposure to drugs, immune reactions, genetically determined sensitivities to certain substances as seen with copper in Wilson's disease and infections such as viral hepatitis, syphilis and various parasitic infections including, but not limited to, Schistosomiasis mansoni and S. japonica. Other examples of infections which may cause such a liver fibrotic condition include, but are not limited to, CMV (cytomegalovirus), EBY (Epstein-Barr virus) and various herpes viruses. Hepatitis may also be caused by autoimmune conditions. Other examples of conditions which feature liver fibrosis include, but are not limited to, primary biliary cirrhosis, primary sclerosing cholansitis, chronic liver rejection, cryptogenic liver fibrosis and congenital liver fibrosis.

The terms "poison" and "toxin" hereinafter refer to substances which are hepatotoxic chemical substances, and therefore which are not normally consumed or introduced into the circulation and which have a harmful effect on the subject upon contact with the subject through introduction into the circulation of the subject, consumption by the subject or introduction to the subject through another route of administration. One non-limiting example of such a hepatotoxic chemical substance is lead.

In addition, such a treatment would also be effective for hepatic fibrotic conditions of unknown or poorly defined etiology. Preferably, the methods of the present invention for the treatment or prevention of hepatic cirrhosis or fibrosis include contact with a hepatotoxic chemical substance as the cause for the hepatic fibrosis or cirrhosis.

Since hepatic fibrosis is a necessary precursor for liver cirrhosis, all of these methods can also be used to treat or prevent liver cirrhosis, in addition to treating or preventing those conditions characterized by liver fibrosis alone.

Examples of conditions which are characterized by liver fibrosis alone include, but are not limited to, periportal fibrosis, presinusiodal fibrosis and postsinusiodal fibrosis.

EXAMPLE 8

Method of Manufacture of a Medicament Containing Halofuginone

The following is an example of a method of manufacturing Halofuginone. First, Halofuginone is synthesized in accordance with good pharmaceutical manufacturing practice. Examples of methods of synthesizing Halofuginone, and related quinazolinone derivatives, are given in U.S. Pat. No. 3,338,909. Next, Halofuginone is placed in a suitable pharmaceutical carrier, as described in Example 6 above, again in accordance with good pharmaceutical manufacturing practice.

It will be appreciated that the above descriptions are intended only to serve as examples, and that many other embodiments are possible within the spirit and the scope of the present invention.

What is claimed is:

1. A method for the treatment of hepatic cirrhosis in a subject, comprising the step of administering to the subject a pharmaceutically effective amount of a compound having a formula:

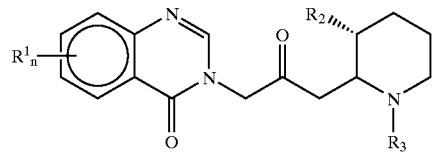

wherein:

$R_1$ is a member of the group consisting of hydrogen, halogen, nitro, benzo, lower alkyl, phenyl, and lower alkoxy;

$R_2$ is a member of the group consisting of hydroxy, acetoxy and lower alkoxy, and $R_3$ is a member of the group consisting of hydrogen and lower alkenoxy-carbonyl;

wherein n is 1 or 2; and pharmaceutically acceptable salts thereof.

2. The method of claim 1, wherein said compound is Halofuginone.

3. The method of claim 1, wherein said compound further includes a pharmaceutically acceptable carrier.

4. The method of claim 1, wherein the hepatic cirrhosis is caused by contact with a hepatotoxic chemical substance.

5. The method of claim 1, wherein the hepatic cirrhosis is caused by a factor selected from the group consisting of chronic alcoholism, malnutrition, hemochromatosis, passive congestion, hypercholesterolemia, exposure to poisons or toxins, exposure to drugs, immune reaction, genetically determined sensitivities to a certain substance, and infections.

6. The method of claim 5, wherein the hepatic cirrhosis is caused by a factor selected from the group consisting of viral hepatitis, syphilis and a parasitic infection.

7. The method of claim 6, wherein said parasitic infection is selected from the group consisting of Schistosomiasis mansoni and S. japonica.

* * * * *